United States Patent
Chu et al.

(10) Patent No.: US 10,426,381 B2
(45) Date of Patent: Oct. 1, 2019

(54) CONNECTORS WITH SWITCHABLE TERMINAL LOADS

(71) Applicant: INTEL CORPORATION, Santa Clara, CA (US)

(72) Inventors: Yunhui Chu, Portland, OR (US); Charles C. Phares, Federal Way, WA (US); John M. Lynch, Forest Grove, OR (US)

(73) Assignee: INTEL CORPORATION, Santa Clara, CA (US)

( * ) Notice: Subject to any disclaimer, the term of this patent is extended or adjusted under 35 U.S.C. 154(b) by 137 days.

(21) Appl. No.: 15/607,333

(22) Filed: May 26, 2017

(65) Prior Publication Data
US 2017/0258372 A1    Sep. 14, 2017

Related U.S. Application Data

(62) Division of application No. 14/757,951, filed on Dec. 26, 2015, now Pat. No. 9,941,643.

(51) Int. Cl.
| | |
|---|---|
| *H01R 29/00* | (2006.01) |
| *A61B 5/117* | (2016.01) |
| *G06F 21/32* | (2013.01) |
| *G06K 9/00* | (2006.01) |
| *G06F 21/83* | (2013.01) |

(52) U.S. Cl.
CPC .............. *A61B 5/117* (2013.01); *G06F 21/32* (2013.01); *G06F 21/83* (2013.01); *G06K 9/00597* (2013.01)

(58) Field of Classification Search
CPC .... H01R 12/73; H01R 12/7094; H01R 12/88; H01R 13/193; H01H 1/5866
USPC .......................................... 439/637, 267, 188
See application file for complete search history.

(56) References Cited

U.S. PATENT DOCUMENTS

| | | | |
|---|---|---|---|
| 3,903,385 A | 9/1975 | Moyer et al. | |
| 4,004,165 A | 1/1977 | Bredael et al. | |
| 4,332,431 A * | 6/1982 | Bobb ..................... | H01R 12/88 439/267 |
| 5,098,306 A | 3/1992 | Noschese et al. | |
| 5,533,907 A | 7/1996 | Kozel et al. | |
| 5,882,217 A | 3/1999 | Aponte et al. | |
| 5,944,546 A | 8/1999 | Miyake et al. | |
| 6,058,444 A | 5/2000 | Johnson | |
| 6,086,426 A | 7/2000 | Chang | |
| 6,105,091 A | 8/2000 | Long | |

(Continued)

OTHER PUBLICATIONS

International Search Report and Written Opinion dated Apr. 21, 2017 for International Application No. PCT/US2016/067049, 10 pages.

(Continued)

*Primary Examiner* — Hae Moon Hyeon
(74) *Attorney, Agent, or Firm* — Schwabe, Williamson & Wyatt, P.C.

(57) ABSTRACT

Switchable grounded terminal loads are built into, or otherwise coupled to, connectors on motherboards and control devices. The terminal loads are coupled to the bus termination at the connector when the connector is "stuffed" (connected to a mating connector). The switchable grounded terminal loads replace dummy connectors in preventing empty "unstuffed" connectors from increasing error risks on active channels.

18 Claims, 7 Drawing Sheets

(56) References Cited

U.S. PATENT DOCUMENTS

| | | | |
|---|---|---|---|
| 6,135,809 A | 10/2000 | Asakawa | |
| 6,174,184 B1* | 1/2001 | Meng | H01R 12/7094 |
| | | | 439/188 |
| 6,918,778 B2 | 7/2005 | Ruckerbauer et al. | |
| 7,029,285 B2* | 4/2006 | Abe | H01R 12/7094 |
| | | | 200/51.1 |
| 7,247,038 B2 | 7/2007 | Smadi et al. | |
| 7,537,473 B2 | 5/2009 | Johannes | |
| 8,179,158 B2 | 5/2012 | Flamm | |
| 8,936,488 B2 | 1/2015 | Bahali et al. | |
| 2003/0049949 A1* | 3/2003 | Abe | H01R 12/7094 |
| | | | 439/61 |
| 2010/0291778 A1 | 11/2010 | Homer et al. | |
| 2012/0033370 A1 | 2/2012 | Reinke et al. | |
| 2014/0153194 A1* | 6/2014 | Bahali | H01R 12/721 |
| | | | 361/728 |
| 2014/0199863 A1 | 7/2014 | Lin | |
| 2014/0199866 A1* | 7/2014 | Tang | H01R 12/7094 |
| | | | 439/159 |
| 2014/0218050 A1 | 8/2014 | Lin et al. | |
| 2017/0187151 A1* | 6/2017 | Chu | H01R 13/7035 |

OTHER PUBLICATIONS

Non-Final Office Action dated May 30, 2017 for U.S. Appl. No. 14/757,951, 12 pages.
Final Office Action dated Jun. 28, 2017 for U.S. Appl. No. 14/757,951, 12 pages.
Non-Final Office Action dated Jul. 3, 2017 for U.S. Appl. No. 15/607,327, 11 pages.

* cited by examiner

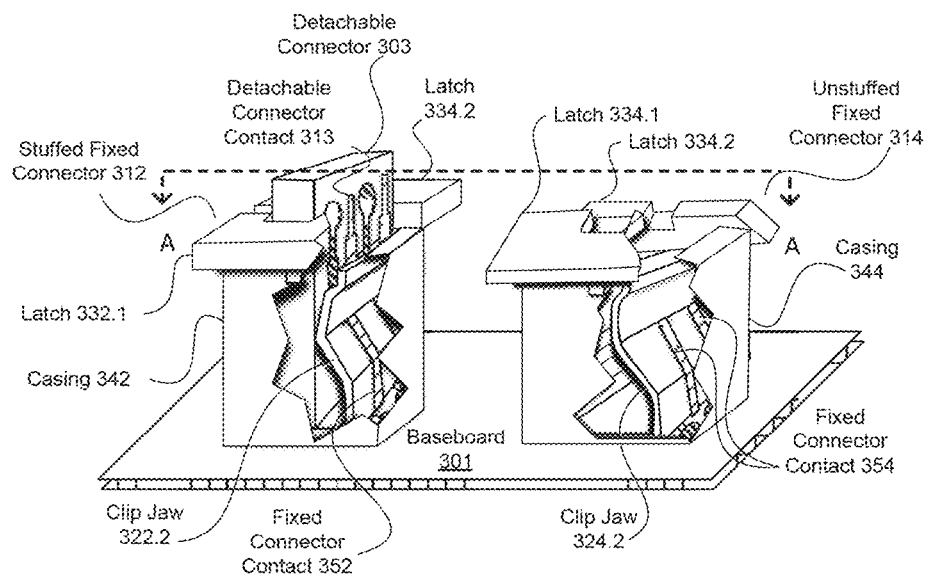
*FIG. 3A*
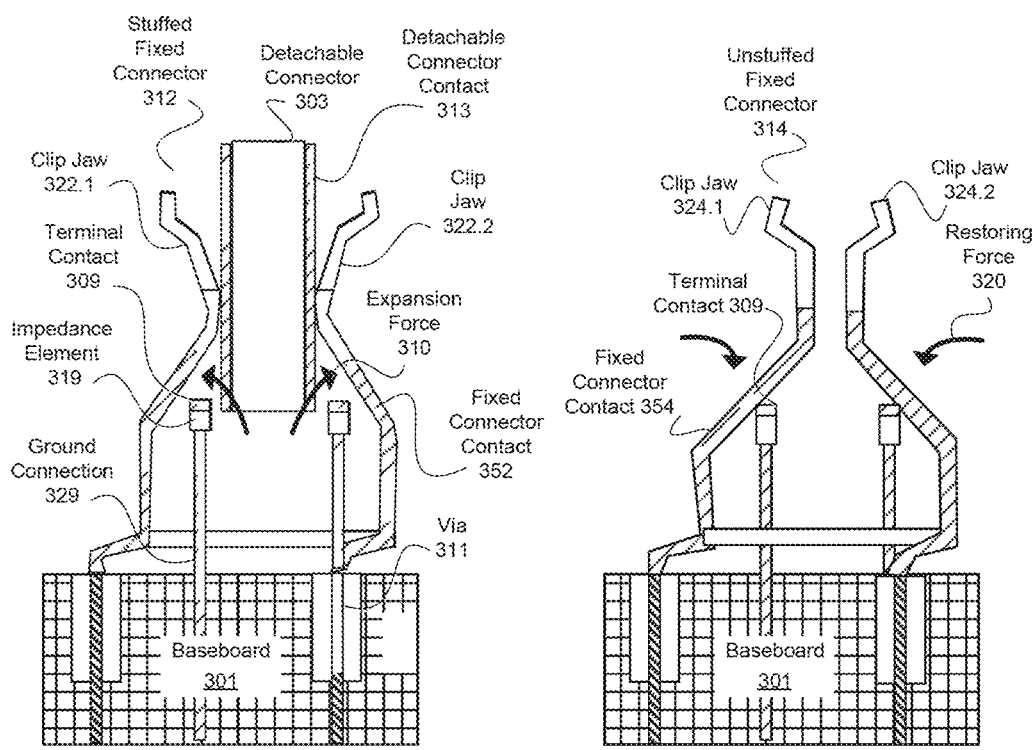
*FIG. 3B*  *FIG. 3C*

CONNECTORS WITH SWITCHABLE TERMINAL LOADS

RELATED APPLICATIONS

This application claims the benefit of priority from U.S. Non-Prov. patent application Ser. No. 14/757,951 filed Dec. 26, 2015 which is entirely incorporated by reference herein.

FIELD

Related fields include electrical connectors, and more particularly techniques for controlling impedance in empty slots, tabs, plugs, or sockets connected to central processing units (CPUs) or other processors or controllers.

BRIEF DESCRIPTION OF DRAWINGS

FIGS. 3A-3C illustrate a terminal load engaged and disengaged by spring forces in a compression clip.

DETAILED DESCRIPTION

For purposes herein, the following terms shall be associated with the following definitions:

Detachable Connector: A connector that can engage to, and disengage from, a Fixed Connector; for example, a tab on a memory card that mates with a slot on a motherboard or a plug at the end of a cable that mates with a socket in a device housing.

Fixed Connector: A connector permanently attached, directly or through a cable, to a controlling component such as a motherboard or a controlling device such as a desktop computer or mobile phone which may or may not be accessible through a device housing.

Computers and electronic devices are made with various fixed connectors both inside and outside the housing. Connectors accessible only from inside the housing provide flexibility for manufacturing, upgrading, and repair. For example, a motherboard may have several expansion slots for memory cards, audio/video cards, networking cards, and the like. The same motherboard may be installed with most of the expansion slots empty in a basic model, or with most of the expansion slots full in a higher-end model. An end user who initially buys a basic model can fill up more of the expansion slots later to improve or expand functionality. If either a card or a slot is damaged, the bad card may be swapped for a good card or the good card may be moved from the bad slot to an empty good slot. Storage devices that can be easily attached to and detached from motherboards provide similar configuration flexibility.

Connectors accessible from outside the housing enable connection of the device to peripheral devices, peer devices, and networks. Portable devices in particular may be connected to, and disconnected from, multiple power sources, display devices, scanners, printers, keyboards, mice, and docking stations several times a day.

In many devices, some of the fixed connectors are likely to be disconnected (empty, or "unstuffed") at any given time. Some systems may tolerate emptiness of some types of fixed connectors, but others may increase noise, degrade signal quality, or cause other problems that would be absent if the connector were connected (occupied, or "stuffed"). Accordingly, passive "dummy" cards or plugs are made for a variety of connector types. They do not add any new functionality to the device, but they provide a terminal load, sometimes with grounding, so that the fixed connector performs as if it were engaged with a detachable connector rather than being empty. Although they remedy some of the problems, dummy cards may add significant cost to the system.

To avoid exposing unconnected pins and plugs to external environments or foreign objects, many fixed connectors may be female, with recessed electrical contacts. However, embodiments of the disclosed concepts may be adapted for fixed male connectors as well as fixed female connectors.

Figure 1:
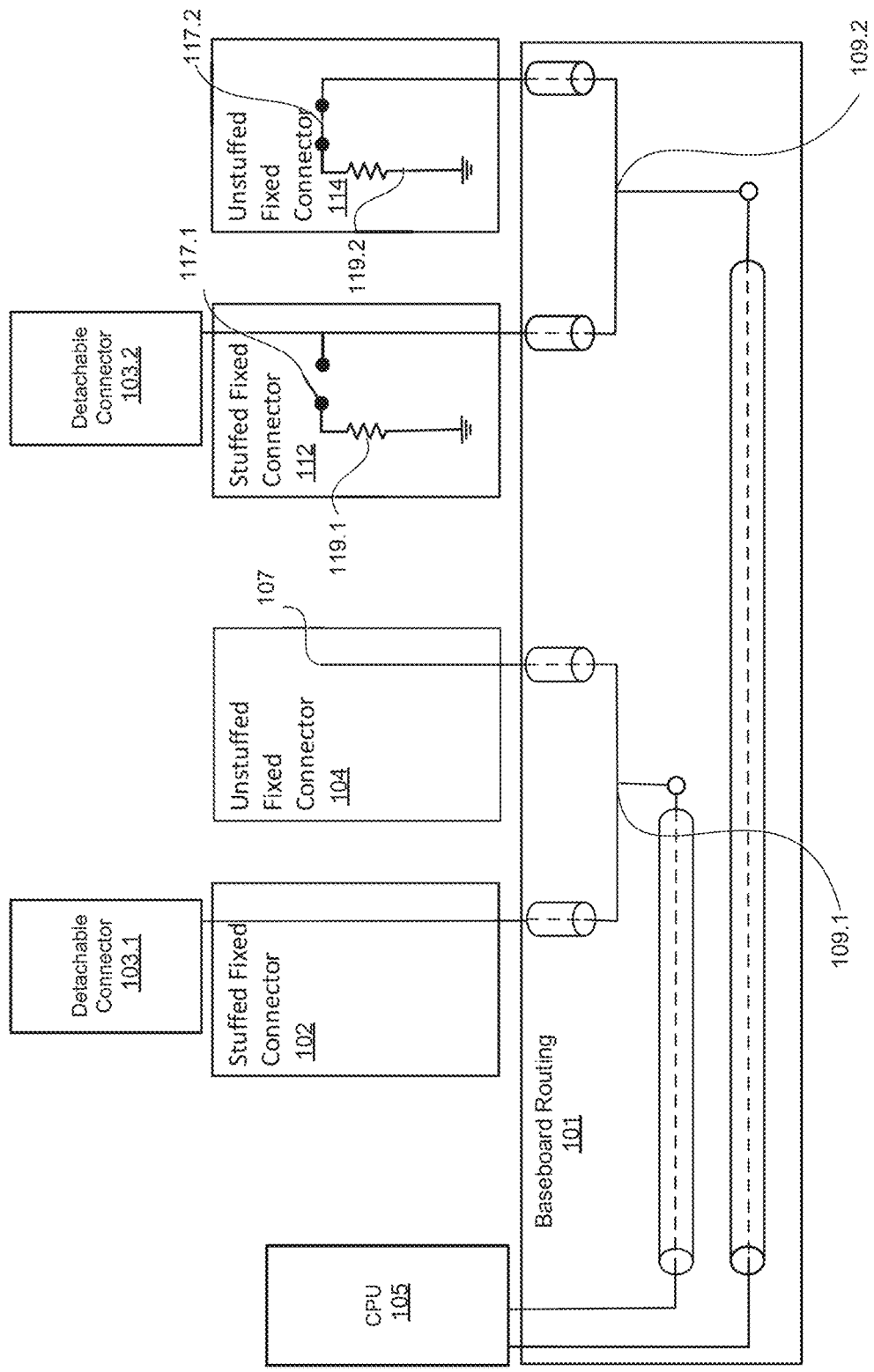
FIG. 1 is a block diagram of stuffed (connected) and unstuffed (empty) fixed connectors on a motherboard.

FIG. 1 is a block diagram of stuffed (connected) and unstuffed (empty) fixed connectors on a motherboard. The baseboard routing 101 is shown connecting the CPU 105 to each of a pair of T-topology buses 109.1 and 109.2.

The branches of T-topology bus 109.1 terminate in one of the simplest fixed connector types. The fixed connector 102 is "stuffed," i.e., a mating detachable connector 103.1 having one or more pins or contacts is engaged with fixed connector 102. The fixed connector 104 is "unstuffed," i.e., empty or unconnected. The absence of a contact leaves termination 107 "floating," i.e., unloaded and ungrounded.

Floating termination 107 may introduce an impedance mismatch that degrades the performance of T-topology bus 109.1 and increases the risk of error for the component connected to CPU 105 by detachable connector 103.1 and stuffed fixed connector 102. For example, some dual in-line memory modules (DIMMs) may have a "Low" (0-1%) risk of write errors and a "Medium" (1-10%) risk of read errors on a T-topology bus 109.1 if both fixed connectors are stuffed, but if one fixed connector is unstuffed the risk of both read and write errors may increase to "High" (10-50%). Changing the design of T-topology bus 109.1 for better performance with one stuffed fixed connector 102 and one unstuffed fixed connector 104 may unsatisfactorily compromise the bus performance with two stuffed fixed connectors while never quite reaching the desired performance level with one stuffed and one unstuffed.

At the terminations of T-topology bus 109.2, stuffed fixed connector 112 and unstuffed fixed connector 114 eliminate floating terminations. Grounded terminal loads 119.1 and 119.2 are switchably coupled to the terminations of T-topology bus 109.2. The switch 117.1 is open when the fixed connector 112 is stuffed with detachable connector 103.2, disconnecting grounded terminal load 119.1 from its branch of T-topology bus 109.2 so that the only connection of stuffed fixed connector 112 is with detachable connector 103.2. Stuffed fixed connector 112 may thus behave like conventional stuffed fixed connector 102. The unstuffed fixed connector 114 has switch 117.2 that is closed so that its termination of T-topology bus 109.2 is connected to grounded terminal load 119.2 instead of floating. The grounded terminal load 119.2 may be designed to match the impedance of detachable connector 103.2 so that T-topology bus 109.2 may behave as if both fixed connectors are stuffed even if one or both fixed connectors are in fact unstuffed.

The grounded terminal loads 119.1, 119.2 are illustrated as schematic resistors, but in some embodiments they may include other types of impedance-matching components, depending on the characteristics of detachable connector 103.2. The grounded terminal loads 119.1, 119.2 and/or switches 117.1, 117.2 may be positioned in, on, or around fixed connectors 112, 114 in any suitable location and orientation. Additionally, in some embodiments, switches 117.1, 117.2 may be actuated by any convenient effect that may be made to coincide with engagement and disengagement of the detachable connector 103.2 from the fixed connector 112. In some embodiments, switches 117.1, 117.2 actuate mechanically, such as by a spring which has the advantage of not requiring any added electrical power to operate the switch.

For example, detachable connector 103.2 may be the connector tab on a memory card, e.g., a DIMM card. In some embodiments, detachable connector 103.2 may be a connector tab for an audio-visual (A/V) card, an option card, a graphics card, a Peripheral Component Interconnect Express (PCIe) card, a PCIe card raiser. In other embodiments, detachable connector 103.2 may be a Serial AT Attachment (SATA) detachable connector. In yet other embodiments, detachable connector 103.2 may be a Universal Serial Bus (USB) plug or a DisplayPort (DP) plug.

Figure 2:
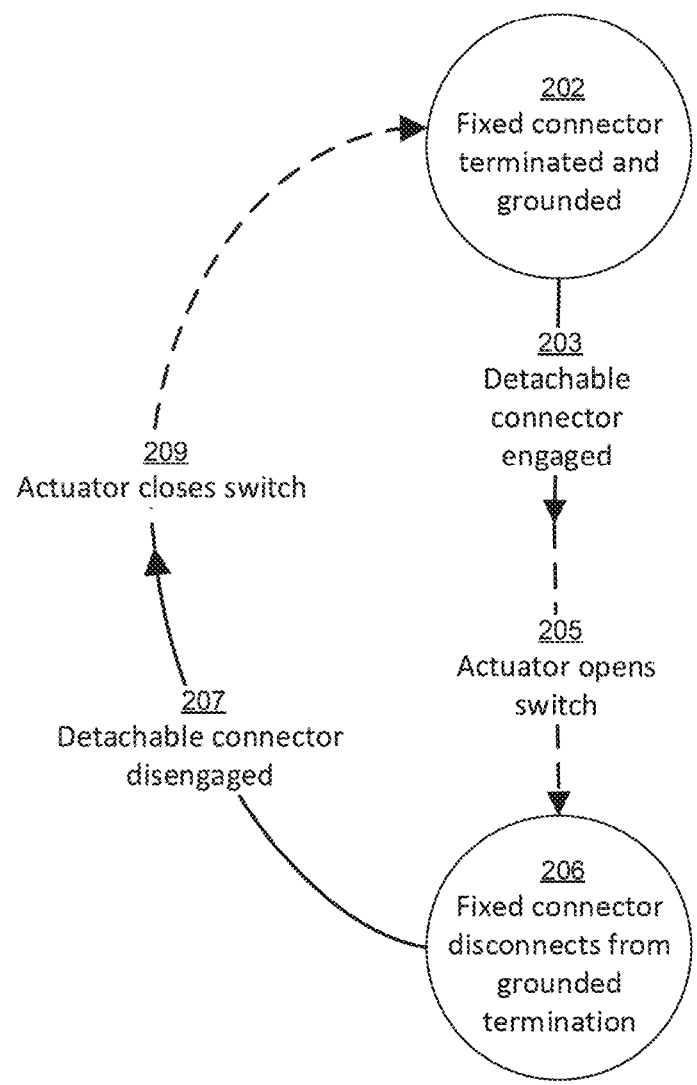
FIG. 2 is a state diagram for a connector with a switchable terminated load.

FIG. 2 is a state diagram for a connector with a switchable terminated load. In state 202 (e.g., when initially installed), the grounded terminal load is engaged by default and the fixed connector is terminated and grounded. State 202 may be a default state whenever the system power is on and the fixed connector is unstuffed. In some embodiments, state 202 may persist when the power is off and the fixed connector is unstuffed, to make it the default power-up state.

Stimulus 203, in which the detachable connector is engaged (optionally followed by stimulus 205, in which an actuator opens the switch), triggers a state change to state 206, in which the fixed connector is disconnected from the grounded terminal load. From there, stimulus 207, in which the detachable connector is disengaged (optionally followed by stimulus 209, in which the actuator closes the switch, triggers a state change back to state 202). The actuator inputs are optional because some embodiments change states without requiring an "actuator" per se as a separate part. In such embodiments, the switching is actuated by a mechanical reaction of existing parts to the insertion or removal of the detachable connector.

FIGS. 3A-3C illustrate a terminal load engaged and disengaged by spring forces in a compression clip. FIG. 3A is a perspective view of stuffed and unstuffed fixed connectors with cutaways to show interior compression clips. These connectors are generic and not intended to represent any particular manufacturer's product. Fixed connectors 312 and 314 are mounted on baseboard 301, which may be, for example, a printed circuit board (PCB). They may be enclosed in casings 342 and 344 with (or, alternatively, without) end latches 332.1, 332.2, 334.1, and 334.2.

Inside the casings 342, 344 (which are shown partially cut away to show the interior structure), the fixed connectors 312 and 314 may include spring-loaded clips with compression jaws 322.2, 324.2. The detachable connector 303 may be a tab extending from another PCB or a packaged module. Clip jaws 322.1, 322.2 of stuffed fixed connector 312 expand to admit detachable connector 303 and exert a compressive restoring force to hold detachable connector 303 securely in place. Latches 332.1 and 332.2 are shown in a horizontal locked position, which also acts to hold the detachable connector in place.

In some embodiments, fixed connectors 312 and 314 may include conductive pins or leads such as fixed connector contacts 352, 354. In stuffed fixed connector 312, fixed connector contacts 352 make electrical contact as well as mechanical contact with detachable connector contacts 313 (e.g., pins or "goldfingers") of detachable connector 303. For simplicity, very short connectors with only a few pins are illustrated, but those skilled in the art understand that the same type of connector may be made in a variety of lengths with varying numbers of pin, strip, or similar connections.

In unstuffed fixed connector 314, the absence of a detachable connector allows clip jaw 324.2 to relax to an equilibrium position angled further toward a longitudinal midplane than the position of clip jaw 322.2. The latches 334.1 and 334.2 are shown tilted outward from the ends, which position allows the detachable connector to be inserted or released.

FIG. 3B is a sectional view of stuffed fixed connector 312 through section A-A of FIG. 3A, omitting the casing. In some embodiments, fixed connector contacts 352 may be connected to vias 311 that extend through one or more layers of baseboard 301. The grounded terminal load for stuffed fixed connector 312 may include terminal contact 309, impedance element 319, and ground connection 329. In some embodiments, ground connection 329 may connect to a ground plane of baseboard 301.

When detachable connector 303 is inserted in the clip, it exerts expansion force 310 on clip jaws 322.1 and 322.2. Clip jaws 322.1 and 322.2 "push back" with a restoring force to hold detachable connector 303 in place, but are held too far apart by detachable connector 303 to touch terminal contacts 309. Therefore, when fixed connector 312 is stuffed, the fixed connector contacts 352 connect only with the detachable connector contacts 313, and the grounded terminal load is unconnected to the fixed connector contacts 352.

FIG. 3C is a sectional view of unstuffed fixed connector 314 through section A-A of FIG. 3A. When detachable connector 303 is absent from the clip, it exerts no expansion force on clip jaws 324.1, 324.2. Without that opposing force, restoring force 320 pushes clip jaws 324.1, 324.2 inward toward their equilibrium position. Somewhere along the path of relaxation of clip jaws 324.1, 324.2, the fixed connector contacts 354 touch terminal contacts 309. Therefore, whenever fixed connector 314 is unstuffed, the restoring force of clip jaws 324.1, 324.2 automatically connects the grounded terminal load 309, 319, 329, terminating the fixed connector contacts 352 so that unstuffed fixed connector 314 does not have a floating termination.

Figure 4A:
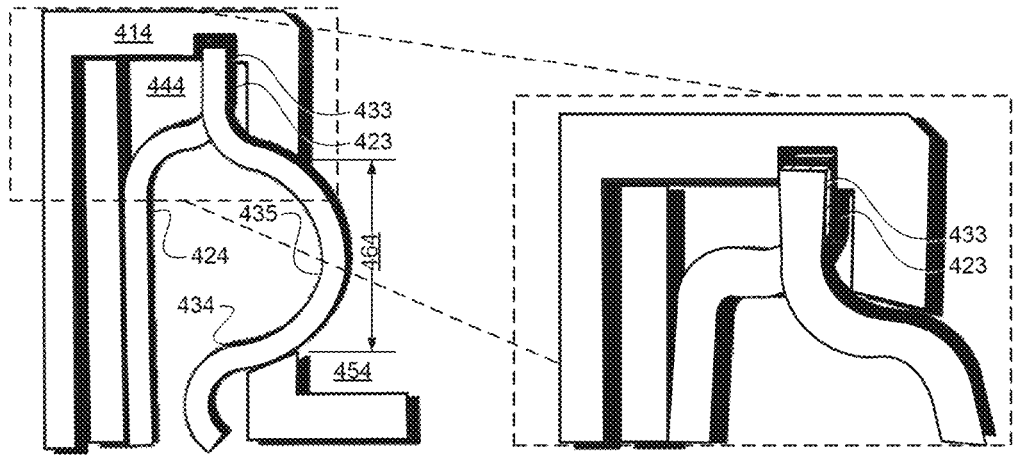
FIGS. 4A-4B are views of a mechanical switch.
Figure 4B:
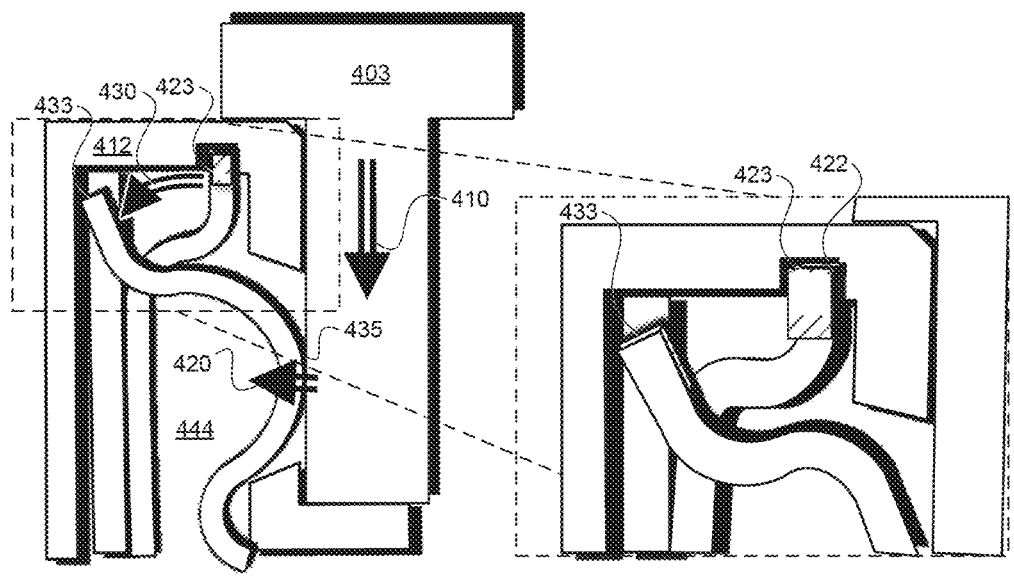

FIGS. 4A-4B are views of a mechanical switch. The switches shown in the figures may be made small enough to build into some types of connectors. FIG. 4A shows two different magnifications of part of an unstuffed fixed connector with the switch closed to connect the terminal load. Unstuffed fixed connector 414 includes a cavity 444. Cavity 444 holds two arms, stationary arm 424 and moveable arm 434, that constitute the switch. The moveable arm 434 has a first conductive contact 433, which in unstuffed fixed connector 414 touches a second conductive contact 423 on stationary arm 424. When the first conductive contact 433 and the second conductive contact 423 are touching, current can flow between stationary arm 424 and moveable arm 434. One of stationary arm 424 or moveable arm 434 may be connected to a grounded terminal load (not shown). Moveable arm 434 also features a bend 435 that protrudes through an opening into receptacle 454 of unstuffed fixed connector 414, where the detachable connector is normally inserted with a running-and-sliding fit or an interference fit, depending on the type of connector.

FIG. 4B shows two different magnifications of part of a stuffed fixed connector with the switch open to disconnect the terminal load. Detachable connector 403 is inserted in the receptacle of fixed connector 412 using downward pressure 410. When detachable connector 403 encounters bend 435 of moveable arm 434, it pushes bend 435 out of the receptacle and back into the cavity in direction 420. Meanwhile, second contact 423 is held in place by locating feature 422 in the cavity wall of the connector body. The rigidity of moveable arm 434, including bend 435, moves the first contact 433 off of and away from second contact 423 in direction 430, thereby opening the switch and disconnecting the grounded terminal load (not shown in this view).

Materials for the first contact and second contact may be any conductive material that can withstand the expected number of couplings and uncouplings over the life of the connector. Gold or silver may be chosen for connectors that are connected and disconnected less often. Copper, aluminum, or harder alloys containing gold or silver may be preferred where connecting and disconnecting will be done more often. The bend and contact-end section of the moveable arm may preferably be a rigid material for repeatable motion while the section of the moveable arm below the bend may either provide an elastic restoring force itself (e.g., work-hardened metal) or be rigid and coupled to a spring that provides the restoring force.

Figure 5:
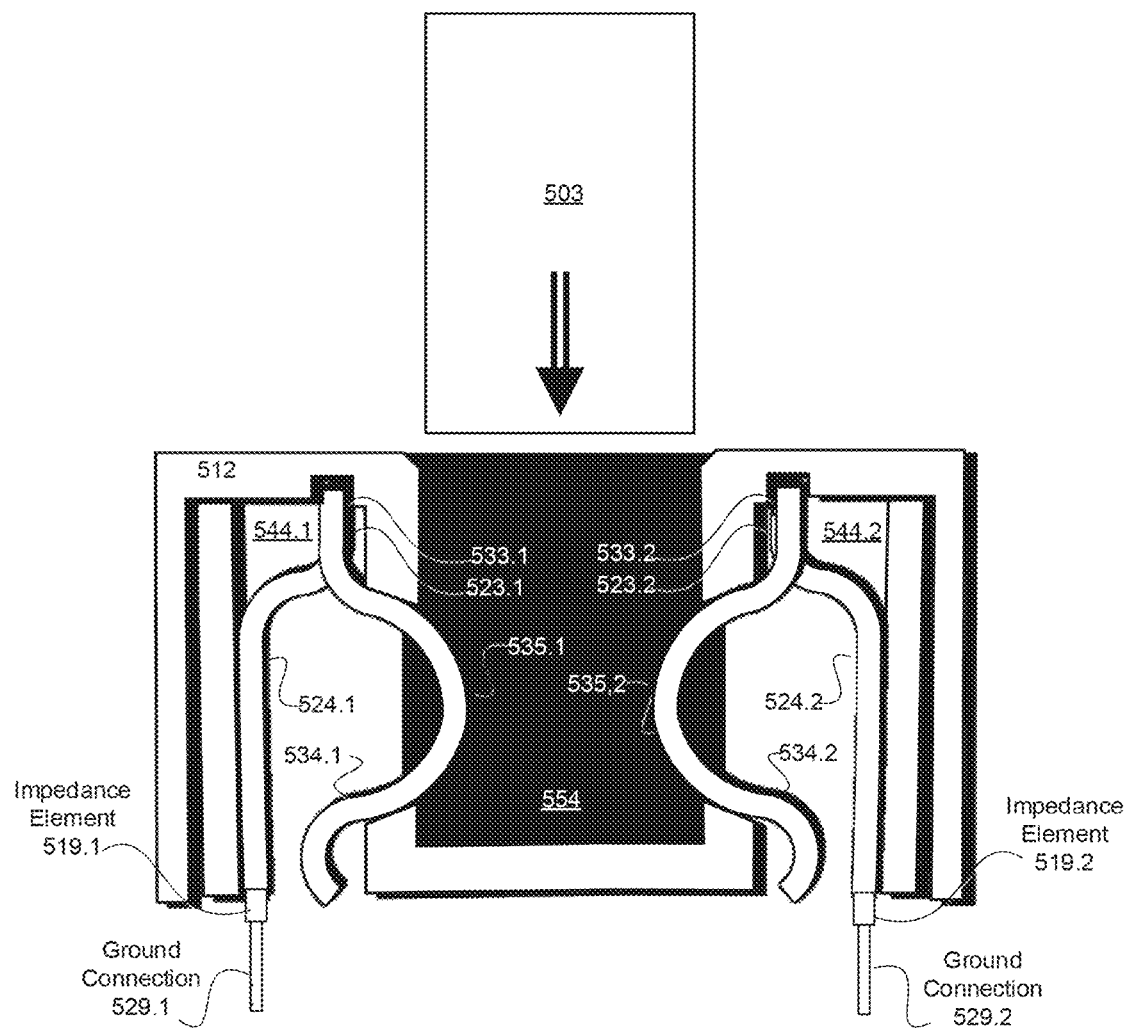
FIG. 5 is a connector with switchable grounded terminal loads on two receptacle walls.

FIG. 5 is a connector with switchable grounded terminal loads on two receptacle walls. The connector 512 has switches on opposing sides of receptacle 554. Alternatively, switches may be on adjacent walls; preference may depend on the location of the bus terminations that benefit from termination loads. Unstuffed connector 512 has a pair of mirror-image cavities 544.1 and 544.2. Each one has a stationary arm 524.1 or 524.2 connected to a terminal load that includes an impedance element 519.1 or 519.2 and a ground connection 529.1 or 529.2. The grounded terminal loads 519.1+529.1, 519.2+529.2 may be coupled to either the stationary arms 524.1, 524.2 or the movable arms 534.1, 534.2. However, in some embodiments, it may be preferable to use the stationary arm 524.1, 524.2 to avoid transferring repeated stresses to the grounded terminal loads 519.1+529.1, 519.2+529.2.

While receptacle 554 is empty, first contacts 533.1 and 533.2 on movable arms 534.1, 534.2 will touch second contacts 523.1 and 523.2 on stationary arms 524.1 or 524.2 to provide electrical couplings to the grounded terminal loads 519.1+529.1, 519.2+529.2. If detachable connector 503 is inserted in receptacle 554, it will displace two bends 535.1 and 535.2 of moveable arms 534.1 and 534.2. When bends 535.1 and 535.2 are pushed back into cavities 544.1, 544.2, first contacts 533.1 and 533.2 on movable arms 534.1, 534.2 will move away from second contacts 523.1 and 523.2 on stationary arms 524.1 or 524.2 to eliminate electrical couplings to the grounded terminal loads 519.1+529.1, 519.2+529.2.

Figure 6:
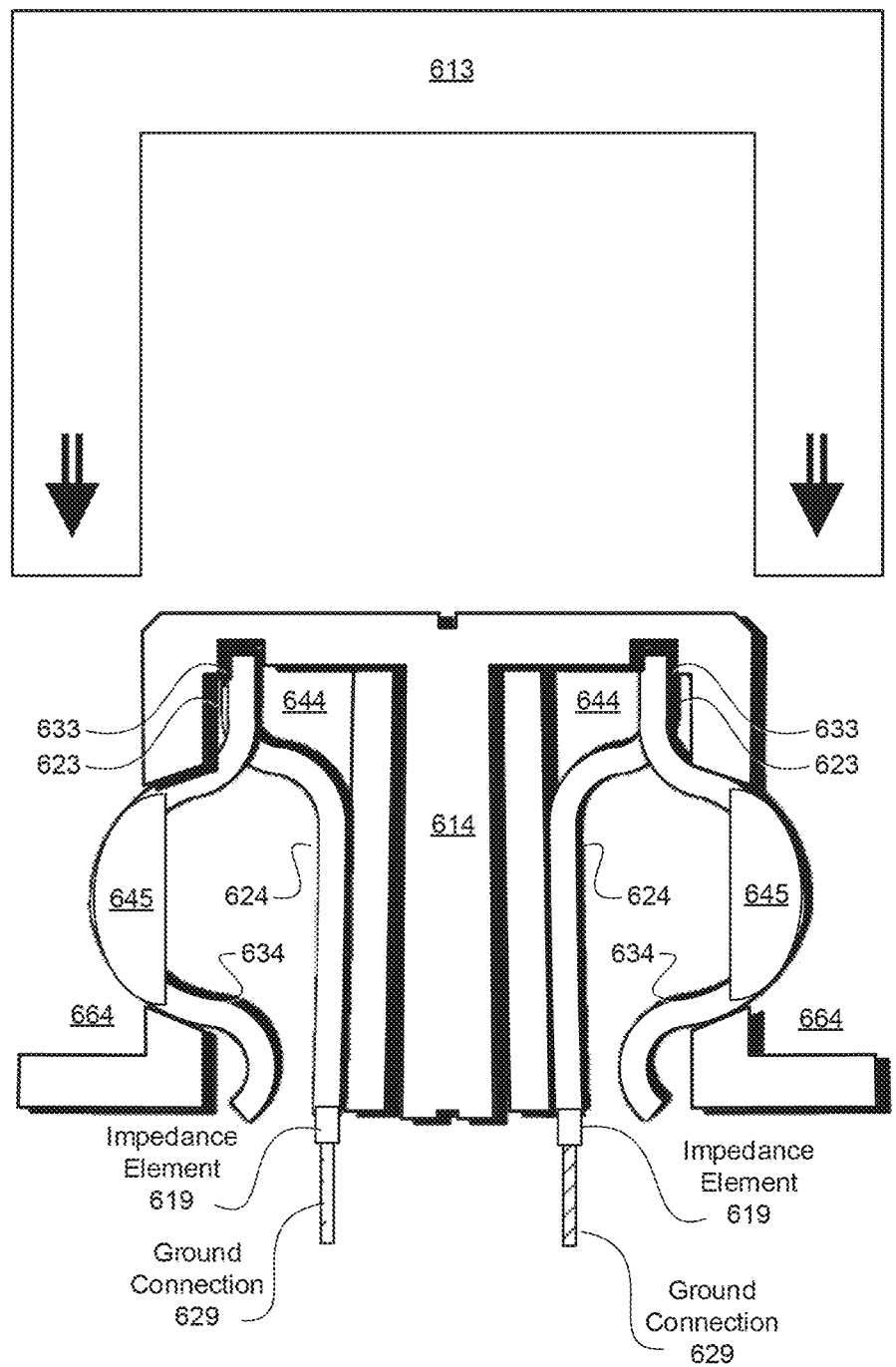
FIG. 6 is an adaptation of the two-switch, two-load schema for male fixed connectors.

FIG. 6 is an adaptation of the two-switch, two-load schema for male fixed connectors. At this writing, a majority of fixed connectors are female because the recessed contacts on a female connector are less exposed, and thereby may be less vulnerable to accidental shorting and other problems. However, the disclosed approach may also work with male fixed connectors.

Connector 614 is a male connector compatible with mating connector 613. Instead of an inner receptacle, the space to be occupied by the mating connector 613 is an outer perimeter 664. The configuration may be very much like FIG. 5—dual mirror-image cavities 644, stationary arms 624, first contacts 623, moveable arms 634, second contacts 633, impedance elements 619, and ground connections 629—except that the bends and openings face outward rather than inward. Bends may be replaced with solid (e.g., molded) tabs 645 in any of the designs.

Figure 7:
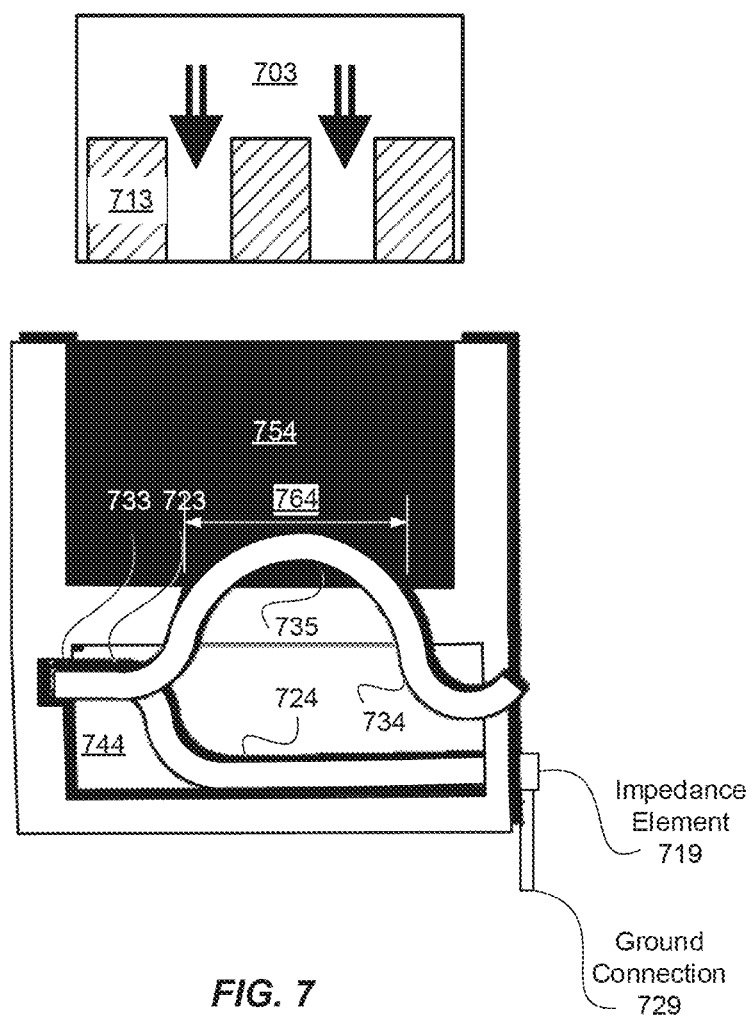
FIG. 7 is a connector with a single switchable terminal load.

FIG. 7 is a connector with a single switchable terminal load. This approach may be especially suitable for slots that mate with tabs 703 with contacts 713 on the side, so that the bottom surface may be used to switch the terminal load, which may include impedance element 719 and ground connection 729. This terminal load is coupled to stationary arm 724 at a right angle. As with the other illustrated examples, bend 735 in moveable arm 734 protrudes into the space for the currently absent mating connector 703, and first contact 733 touches second contact 723 to close the switch and couple the bus termination(s) to the terminal load. When inserted, mating connector 703 will push bend 735 down to move first contact 733 away from second contact 723 to decouple the connector from the grounded terminal load.

Non-limiting examples of the types of connectors that could potentially be customized with switchable terminal loads include Peripheral Component Interconnect Express (PCIe), USB, DisplayPort, SATA, raiser, option cards, and AN boards. Models predicted that connectors with switchable terminal loads yield about the same error rate as connectors with more expensive dummy mating connectors installed.

The preceding Description and accompanying Drawings describe examples of embodiments in some detail to aid understanding. However, the scope of protection may also include equivalents, permutations, and combinations that are not explicitly described herein. Only the claims appended here (along with those of parent, child, or divisional patents, if any) define the limits of the protected intellectual-property rights.

We claim:

1. An apparatus, comprising:
    a pair of spring-loaded members including a first spring-loaded member, the first spring-loaded member including a compression part at one end, a board contact at another end to be in contact with a baseboard, and a fixed connector contact between the compression part and the board contact; and
    a stationary member to be in contact with the baseboard, the stationary member including at least one terminal load,
    the pair of spring-loaded members to expand to an expanded position to admit a detachable mating connector and to exert a compressive restoring force on the detachable mating connector,
    the pair of spring-loaded members to return to an equilibrium position when the detachable mating connector is not present,
    wherein, in the equilibrium position, the fixed connector contact of the first spring-loaded member is in contact with the stationary member including the at least one terminal load, and
    wherein, in the expanded position, neither of the pair of spring-loaded members is in contact with the stationary member including the at least one terminal load.

2. The apparatus of claim 1, wherein the at least one terminal load is disposed between the pair of spring-loaded members.

3. The apparatus of claim 1, wherein the pair of spring-loaded members comprise a conductive material; and wherein the at least one terminal load comprises a conductive contact that touches one of the pair of spring-loaded members to connect the at least one terminal load.

4. The apparatus of claim 3, wherein the pair of spring-loaded members comprise conductive pins or leads.

5. The apparatus of claim 1, wherein the pair of spring-loaded members comprise a spring-loaded clip with a compression jaw.

6. The apparatus of claim 1, wherein the at least one terminal load comprises an impedance-matching component.

7. The apparatus of claim 1, wherein the at least one terminal load comprises a resistor.

8. The apparatus of claim 1, wherein the at least one terminal load comprises a ground connection to be coupled to a ground plane of the baseboard.

9. The apparatus of claim 1, further comprising:
latches to hold the detachable mating connector in place.

10. The apparatus of claim 1, further comprising:
a casing to hold the pair of spring-loaded members and the at least one terminal load inside the casing.

11. An apparatus, comprising:
a pair of spring-loaded clips with compression jaws including a first spring-loaded clip, the first spring-loaded clip including a compression jaw at one end, a board contact at another end to be in contact with a baseboard, and a fixed connector contact between the compression jaw and the board contact; and
a stationary member to be in contact with the baseboard, the stationary member including a terminal load,
the pair of spring-loaded clips with compression jaws to expand to an expanded position to admit a detachable connector,
the pair of spring-loaded clips with compression jaws to return to an equilibrium position when the detachable connector is not present,
wherein, in the equilibrium position, the fixed connector contact of the first spring-loaded clip is in contact with the stationary member including the terminal load, and
wherein, in the expanded position, neither of the pair of spring-loaded clips with compression jaws is in contact with the stationary member including the terminal load.

12. The apparatus of claim 11, wherein the pair of spring-loaded clips with compression jaws comprise conductive pins or leads.

13. The apparatus of claim 11, wherein the fixed connector contact of the first spring-loaded clip is coupled to a via that extends through one or more layers of the baseboard.

14. The apparatus of claim 11, wherein the terminal load comprises an impedance-matching component.

15. The apparatus of claim 11, wherein the terminal load comprises a resistor.

16. The apparatus of claim 11, wherein the terminal load comprises a ground connection to be coupled to a ground plane of the baseboard.

17. The apparatus of claim 11, further comprising:
latches to hold the detachable connector in place.

18. The apparatus of claim 11, further comprising:
a casing to hold the pair of spring-loaded clips with compression jaws and the terminal load inside the casing.

* * * * *